United States Patent [19]

Cronyn

[11] Patent Number: 4,950,768
[45] Date of Patent: Aug. 21, 1990

[54] CYCLIC DISULFONIC ESTER CROSS-LINKING COMPOUNDS

[76] Inventor: Marshall W. Cronyn, 3232 NW. Luvay Ter., Portland, Oreg. 97210

[21] Appl. No.: 570,786

[22] Filed: Jan. 16, 1984

[51] Int. Cl.$^5$ ............................................. C07D 339/00
[52] U.S. Cl. ........................................ 549/11; 556/428
[58] Field of Search ........................................... 549/11

[56] References Cited

U.S. PATENT DOCUMENTS 4,483,799  11/1984  Kampfer et al. ................. 260/456 R

FOREIGN PATENT DOCUMENTS 0210874  8/1960  Austria .................................. 549/11
1124032  2/1962  Fed. Rep. of Germany ... 260/456 R
1277247  9/1968  Fed. Rep. of Germany ........ 549/11
0700677  12/1953  United Kingdom ........... 260/456 A

OTHER PUBLICATIONS

Remers, W. A., "Antineoplastic Agents", John Wiley & Sons, New York, N.Y., 1984, pp. 69–76.
Hecht, A., "Cancer Drugs That Work", FDA Consumer, Oct., 1977, pp. 18, 20, 21.
Hayashi et al., Chemical and Pharmaceutical Bulletin, vol. 12, No. 11, 1964, pp. 1271–1272.
Leong, "Synthesis of Cyclic Methanedisulfonate Esters by the Silver Salt Method", Reed College Chemistry Library, 1972.
Engel, "Synthesis of Cyclic Methanedisulfonate by Diol Reaction Method", Reed College Chemistry Library, 1981.
McCaffrey, "Synthesis of Cyclic Methanedisulfonates: Analogues of Myleran–A Cancer Chemotherapy Compound", Reed College Chemistry Library, 1982.

*Primary Examiner*—John M. Ford
*Attorney, Agent, or Firm*—Peter J. Dehlinger

[57] ABSTRACT

Cyclic disulfonic ester bifunctional cross-linking compounds effective in treating certain types of cancers are described. Initial nucleophilic reaction with the compound produces a negatively charged sulfonic acid end-group which remains attached to the compound until the second nucleophilic crosslinking reaction occurs.

6 Claims, No Drawings

CYCLIC DISULFONIC ESTER CROSS-LINKING COMPOUNDS

BACKGROUND OF THE INVENTION

The present invention relates to bifunctional cross-linking compounds; in particular, to cyclic disulfonic ester cross-linking compounds.

Alkylating agents are a major class of cancer chemotherapeutic compounds. Most clinically used alkylating agents are bifunctional compounds having two chemically reactive centers capable of reacting with and cross-linking biomolecules, such as the opposite strands of duplex DNA. Use of these agents to alkylate biomolecules leads to a variety of defects in intracellular metabolism, particularly defects in nucleic acid replication and/or transcription, which tend to be more lethal in rapidly growing cancer cells than in normal somatic cells.

Busulfan (Myleran, Burroughs Wellcome) is a bifunctional alkylating agent which is commonly used in the treatment of leukemias, *Guide to Therapeutic Oncology*, Bergevin, P.R., et al., eds., Williams and Wilkins, Baltimore/London (1979), p. 110. This compound is a linear methanesulfonic ester of 1,4-butanediol which functions by forming a butane cross-link between a pair of nucleophiles, such as the 7-position guanine nitrogens in opposite strands of duplex DNA. Initial nucleophilic attack at one of the butane end-carbons in the compound releases a negatively charged methanesulfonic acid group, leaving an uncharged methanesulfonic ester of 1-butanol attached to the nucleophile. A second nucleophilic attack on the opposite butane end-carbon results in cross-linking through the butane moiety, and release of a second negatively charged methanesulfonic acid group. Busulfan is more effective therapeutically than other linear disulfonic esters having cross-linking alkane moieties which are either shorter or longer than butane.

The present invention includes cyclic disulfonic esters having the general structural formula:

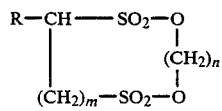

where m=0 or 1, n=1-5, and R=H, CH$_3$, CH$_3$CH$_2$ or Cl. The compounds of the invention are useful as bifunctional agents for cross-linking a variety of nucleophile-containing biomolecules, such as proteins and nucleic acids. The cyclic disulfonic ester in which m=0, n=2 and R=H is effective in the treatment of a variety of mice cancers, including lymphocytic leukemia, lymphoid leukemia, melanocarcinoma, human breast xenograft and ovarian carcinoma. Cyclic disulfonic esters in which m=0, n=3 or 4 and R=H have also been shown to have anti-leukemic activity.

Unlike Busulfan-type linear disulfonic esters where the butanediol (n=4) diester is most therapeutically effective, among cyclic compounds of the present invention, the disulfonic ester of ethanediol (n=2) appears to be the most active in treating leukemic animals. The cyclic esters of the present invention are also shown herein to be effective in treating a variety of cancer types other than leukemias, particularly melanocarcinomas, breast xenografts and ovarian carcinomas.

Also unlike uncharged linear alkane disulfonates such as Busulfan, initial nucleophilic attack on a cyclic diester compound of the invention, in opening the diester ring, results in a linear sulfonate having a charged sulfonic acid end-group which remains attached to the compound. The charged end group has the capacity to affect both the solubility of the compound and its configuration in relation to the alkylated biomolecule, in the reaction period between the two nucleophilic cross-linking reaction events.

The invention further includes methods for synthesizing cyclic disulfonic ester compounds of the type described. In one method, useful particularly for synthesizing the n=1 cyclic disulfonic ester of the above structure, an alkanedisulfonyl chloride is allowed to react with a silver salt to form the corresponding silver disulfonate, which is then allowed to react with a dihaloalkane, such as dibromoethane or diiodomethane. In a second method, useful in the preparation of n=2-5 compounds, an alkanedisulfonyl chloride is allowed to react directly with an alkanediol in the presence of an alphatic or aromatic tertiary amine, such as triethylamine or collidine. The tertiary amine is added dropwise to the other reactants at a low temperature to avoid alkylation of the amine by the product ester.

A general object of the invention is to provide a new class of cross-linking compounds which are therapeutically effective in the treatment of several types of cancers.

Another object of the invention is to provide a disulfonic ester bifunctional cross-linking agent capable of reacting with a first nucleophile to produce a nucleophile-reactive agent having a sulfonic acid end group.

Yet another object of the invention is to provide a class of cyclic bifunctional alkylating compounds which are readily synthesized in yields suitable for drug testing and manufacture.

These and other objects and features of the present invention will become more fully apparent from the following detailed description of the invention and accompanying examples.

DETAILED DESCRIPTION OF THE INVENTION

The cyclic disulfonic esters of the present invention are synthesized according to novel methods described below in Section I. Section II describes the reaction of cyclic disulfonic esters with duplex DNA to form cross-linked DNA strands or DNA strands cross-linked to DNA-associated protein. The section also considers a linear disulfonic ester having charged sulfonic acid end groups. This compound may react with duplex DNA in a manner similar to that of the cyclic compound in a cross-linking reaction. A method of synthesis of the linear charged cross-linking agent is also described. Various drug treatment regimens in which selected cyclic disulfonic ester compounds are employed in the treatment of five different types of mammalian cancers are outlined in Section III.

I. Synthesis of Disulfonic Ester Cross-Linking Agents

The present invention includes cyclic disulfonic esters having the general structural formula:

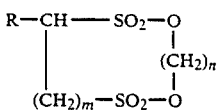

where m=0 or 1, n=1–5, and R=H, CH$_3$, CH$_3$CH$_2$, or Cl.

The first synthetic method to be considered is particularly suitable for the synthesis of compounds of this type in which n=1. The method generally includes allowing an alkane disulfonyl chloride of the form:

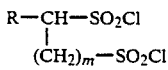

where m and R are as indicated above, to react with a silver salt, preferably silver carbonate, under conditions which produce the corresponding silver disulfonate. Experimentally, the reaction is preferably carried out in the dark under completely anhydrous conditions. An alkane disulfonylchloride, such as methanedisulfonyl chloride, is dissolved in a suitable solvent, such as acetonitrile, and to this solution is added a silver salt, such as silver carbonate, in a molar ratio of slightly more than two moles of silver per mole of the disulfonyl chloride. The mixture is kept below 40° C. bring the initial exothermic reaction and is then stirred at room temperature for 24 hours. The silver chloride powder which forms is removed by filtration. The reaction method, which is described in Example I below, yields approximately 88.5% of the theoretical yield of silver methanedisulfonate.

In the second step of the synthesis, the freshly prepared silver alkanedisulfonate is allowed to react with a dihalide of the form:

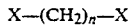

where n=1–4 and X is either bromide or iodide. By way of illustration, silver methanedisulfonate dissolved in a suitable solvent, such as acetonitrile, is added to the dihalide, in approximately a 1 to 1 molar ratio, and the mixture is allowed to stand for up to several weeks at room temperature or is heated under reflux for up to several days in the absence of light. The precipitated silver salt is filtered and the filtrate is evaporated under reduced pressure, leaving a typically light brown, oil-like residue containing the desired product. The residue is dissolved in a suitable solvent, such as methylene chloride, and may be treated with a purifying agents such as decolorizing charcoal added to the solvent. To crystallize the product, a second solvent, such as cyclohexane, is added until a cloudy supernatant forms. Recrystallization in a solvent system such as cyclohexane:methylene choloride 2:1 may be carried out to achieve a desired purity. The identity of the product can be confirmed by characteristic infrared (IR) features, such as CH$_2$ and SO$_2$ stretching frequencies, and by proton nuclear magnetic resonance (NMR) features, such as the resonance positions of the CH$_2$—SO$_2$ proton, the end—CH$_2$—O proton and the middle CH$_2$ proton. Comparing experimental product elemental analysis with theoretical values provides further product-identity confirmation.

Example II describes the preparation of tetramethylene methanedisulfonate (m=0, n=4, R=H), also named 1,5,2,4-dioxadithionane-2,2,4,4-tetroxide, from 1-4 dibromobutane and silver methanedisulfonate. The procedure yielded, upon recrystallization, small white needles whose final weight represented an approximately 3.79% total yield. In Example III, the preparation of trimethylene methanedisulfonate (m=0, n=3, R=H), also named 1,5,2,4-dioxadithiocane-2,2,4,4-tetroxide, from silver methanedisulfonate and 1,3-dibromopropane is detailed. An approximate 11% yield of small white crystals identified as trimethylene methanedisulfonate was obtained. Example IV describes the synthesis of ethylene methanedisulfonate (m=0, n=2, R=H), also named 1,5,2,4-dioxadithiepane-2,2,4,4-tetroxide, from 1,2-dibromoethane and silver methanedisulfonate. Alternative procedures described in this example gave yields, upon recrystallization in a cyclohexane-methylene chloride mixture, of 2.18% and 2.78%. The method of synthesis of methylene methanedisulfonate (m=0, n=1, R=H), also named 1,5,2,4-dioxadithiane-2,2,4,4-tetroxide, is described in Example V, and includes allowing silver methanedisulfonate to react in acetonitrile with an approximately equal molar amount of diiodomethane. A total product yield of about 2.22% was obtained.

A second general method for the synthesis of the novel cyclic disulfonate esters is particularly suitable for compounds whose structures correspond to those in which m=0 and n=2–5, and R=H or CH$_3$. The method generally includes adding a diol of the form:

where n=2–5, to a solvent such as tetrahydrofuran or the dimethyl ether of ethylene glycol (glyme), and adding to this solution, in the same solvent, an approximately equal molar amount of an alkanedisulfonyl chloride of the form:

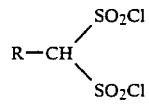

where R=H or CH$_3$. The mixture is cooled to at least about −20° C. and an aliphatic or aromatic tertiary amine is added dropwise to the mixture. Preferred tertiary amines include triethylamine and collidine, a tertiary aromatic amine. The reaction mixture is allowed to warm to 0° C. or slightly higher and the hydrochloride salt which forms is removed by filtration. The filtrate is evaporated under reduced pressure, and the residue, which generally includes a light yellow oil, is dissolved in a suitable solvent, such as methylene chloride. A light crystalline powder, representing the desired recrystallized product, is obtained by crystallization in a suitable solvent system such as methylene chloride:cyclohexane. The identity of the product may be confirmed by characteristic IR and NMR features, such as those mentioned above, and by elemental analysis.

Example VI below describes the synthesis of pentamethylene methanedisulfonate (m=0, n=5, R=H), also named 1,5,2,4-dioxadithiecane-2,2,4,4-tetroxide, according to the just-described method. A solution of 1-5-pentanediol in glyme was mixed with methanedisulfonyl chloride in the same solvent, and to this mixture was added triethylamine dropwise under anhydrous conditions. After removing the amine hydrochloride residue and evaporating the solvent, the oily residue was redissolved in methylene chloride, washed with 3 different aqueous wash solutions, and crystallized from a methylene chloride:cyclohexane solvent system. The procedure gave an approximately 6.75% yield of pure product. Examples VII and VIII describe similar reaction procedures for the synthesis of ethylene methanedisulfonate (m=0, n=2, R=H) from ehtylene glycol and methanedisulfonyl chloride in tetrahydrofuran, with the dropwise addition of collidine. A 25% yield of recrystallized product was obtained. Examples IX and X describe similar reaction methods for producing trimethylene and tetramethylene methanedisulfonate, respectively.

Examples XI–XIV describe the synthesis of 1,1-ethanedisulfonates (m=0, R=CH$_3$) in which n=5 (Example XI), n=4 (Example XII), n=3 (Example XIII) and n=2 (Example IX). It is noted that the cyclic disulfonate compound in which n=1 cannot be synthesized by the present synthetic method. In Example XI, a 2% product yield of pentamethylene 1,1-ethanedisulfonate, was formed. In Example XII, a 9.2% product yield of purified tetramethylene 1,1-ethanedisulfonate, was obtained. The method of Example XIII gave an approximately 36% product yield of the trimethylene 1,1-ethanedisulfonate, and Example XIV produced a 25% product yield of purified ethylene 1,1-ethanedisulfonate.

It will be appreciated from the examples that the general synthetic methods described can be modified readily, particularly with respect to the alkanedisulfonyl chloride starting material, to produce compounds having various indicated R groups and m values.

II. The Cyclic Disulfonate Ester Cross-Linking Reaction

The cyclic disulfonic ester compound of the present invention has a chemically reactive center at each of the CH$_2$—O group carbons, which is capable of reacting with a nucleophile-containing biomolecule. The initial alkylation reaction between a first nucleophile, designated —N$_1$, and the cyclic disulfonic ester results in the formation of a linear complex of the form:

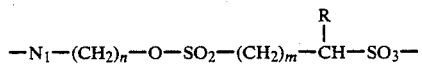

having a negatively charged SO$_3$ end-group. It can be appreciated that the linearized alkylating agent has markedly different solubility and charge characteristics from those of the cyclic compound. It is expected that these charge and solubility characteristics will affect the configuration which the compound adopts with respect to the alkylated biomolecule. In particular, the charged end group may interact with positively charged histones associated with duplex DNA. Preliminary experiments conducted in support of the present invention indicate that the cyclic ethylene disulfonic ester (n=2) is active in cross-linking DNA strands with DNA-associated proteins. The linearized charged complex then undergoes a second nucleophilic reaction, with a nucleophile N$_2$, at its second end-carbon CH$_2$, forming a cross-linked-N—(CH$_2$)$_n$—N$_2$ complex, and releasing a doubly charged alkanedisulfonic acid reaction product.

The present invention more generally contemplates disulfonic esters which are characterized by a sulfonic acid end-group after an initial alkylation reaction. A class of linear disulfonic esters having this property have the general structural formula:

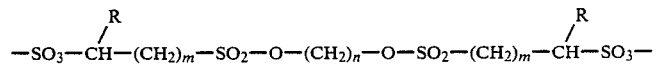

where m=0, n=1–5 and R=H, CH$_3$, CH$_3$CH$_2$ or Cl. With reference to this structure, it can be appreciated that initial nucleophilic attack by a nucleophile N$_1$ at an O—CH$_2$ carbon, produces an N$_1$-alkylating agent complex which is identical to the complex formed after the initial nucleophilic reaction involving the corresponding cyclic disulfonic ester.

Example XV below outlines a procedure for the synthesis of 1,2-bis(oxysulfonylmethanesulfonic acid)ethane (m=0, R=H, n=2). In the method, methanedisulfonyl chloride is allowed to react with water in the presence of diethyl ether to produce the corresponding chlorosulfonylmethanesulfonic acid. The sulfonic acid group in this chemical intermediate is protected by reaction with trimethylsilyl chloride or t-butyldimethylsilyl chloride, according to known procedures. The compound is then allowed to react with ethylene glycol in a suitable solvent, such as glyme, with the addition of an aromatic or aliphatic tertiary amine such as triethylamine dropwise at −20° C. The product is treated with H$_2$O and bicarbonate salt to hydrolyze the silyl esters in the compound, forming the desired salt of the product

III. Anti-Cancer Activity of Cyclic Methanedisulfonate Esters

The effectiveness of cyclic methanedisulfonate esters against various types of mammalian cancers was studied. Individual strains of mice identified as having one of the following types of cancer were employed in the study: lymphocytic leukemia, lymphoid leukemia, melanocarcinoma, human breast xenograft and ovarian carcinoma. For each type of cancer, a group of animals all of about the same size and weight were treated with one of a number of increasing dose levels of the test drug, to identify optimal dosage levels, a evidenced by either maximum survival period or inhibition of tumor growth.

In each test, animals were divided into two equal-number groups: a control group which received the drug carrier alone; and the treated group which received the drug, at optimal dose levels in the drug carrier. In the studies involving lymphocytic leukemia, lymphoid leukemia, melanocarcinoma, and ovarian carcinoma, drug effectiveness was measured by the ratio of median number of days the treated animal survived (T) to the median number of days the control animal survived (C), designated the T/C ratio. Drug effectiveness against human breast xenograft was measured by the ratio of tumor size for treated (T) to tumor size for control (C) animals.

The treatment protocol and results obtained for ethylene methanesulfonate drug treatment are described in Example XVI. The data show that ethylene methanesulfonate substantially prolongs survival time or inhibits tumor growth for all types of cancers which are reported in the example.

Two additional groups of mice having lymphocytic leukemia were treated with either trimethylene methanedisulfonate (n=3) or tetramethylene methanedisulfonate (n=4) for purposes of comparing the therapeutic effectiveness of cyclic disulfonic ester compounds having n=2-4 cross-linking chain lengths. The test conditions and protocol are substantially like those employed in the Example XVI tests, and are described in Examples XVII and XVIII, respectively, for the n=3 and n=4 compounds. Both the trimethylene and tetramethylene methanedisulfonate compounds showed significant anti-leukemic activity, as measured by their T/C ratios, but both were substantially less effective than the cyclic ethylene methanedisulfonate ester in prolonging survival in leukemic animals.

From the foregoing, it can be appreciated how various objects of the invention are met. The cyclic disulfonic esters described herein provide a new class of cross-linking agents whose structure and reaction are quite different from uncharged, linear Busulfantype disulfonic esters.

The compounds of the invention are readily synthesized by one or both of the methods detailed herein, and for several of the compounds, product yields greater than about 25% may be achieved.

The following examples illustrate various methods of synthesis and treatment protocols associated but are not intended to limit the scope of the invention.

EXAMPLE I

Preparation of Anhydrous Silver Methanedisulfonate

Completely anhydrous and dark conditions were employed throughout the preparation. All glassware was baked in an oven at 110° C. for at least one-half hour. Methanedisulfonyl chloride was synthesized according to known methods; See, e.g., G. Schroeter, Ann. Chem. 418, 161-257 (1919). Redistilled methanedisulfonyl chloride (2.00 g, 0.009 mole), was transferred in 15 ml of acetonitrile obtained from Burdick and Jackson Laboratories (Muskegon, MI) to an equalizing dropping funnel. The acetonitrile was dried by distillation over $P_2O_5$. Analytical grade silver carbonate obtained from J.T. Baker Chemical Co. (Phillipsburg, NJ) (99.8%) was weighed (5.22 g, 0.019 mole) and placed into a three-neck flask fitted with an equalizing funnel, a reflux condenser with a drying tube, and a thermometer. A stir bar was added and the disulfonyl chloride solution was allowed to drop in slowly. The mixture became warm and a gas was evolved. The temperature was kept below 40° C. in an ice-water bath. The stir bar was started as soon as possible and the mixture was stirred at room temperature for approximately 24 hours. The reaction mixture was filtered, yielding a light purple powder containing silver chloride and unreacted silver carbonate. The weight of the dried powder was 2.99 g, 0.29 g over the theoretical weight of silver chloride assuming complete reaction of the silver carbonate. Based on these numbers, the yield of silver methanedisulfonate in the filtrate was calculated to be about 88.5%.

EXAMPLE II

Preparation of Tetramethylene Methanedisulfonate

Purified 1,4-dibromobutane obtained from Aldrich Chemical Co. (Milwaukee, WI) (2.03 g, .009 mole) was added to a flask containing 100 ml of freshly prepared solution of silver methanedisulfonate in acetonitrile from Example I. The flask was stoppered and placed in the dark at room temperature for a period of 8 weeks, during which a yellow-green precipitate formed and settled to the bottom of the flask. The suspension was filtered, and the filtrate was washed with dry acetonitrile, leaving silver bromide in suspension. The suspension was filtered and the filtrate dried as in Example I. The dried weight of the filtrate was 2.34 grams, or 67.7% of the theoretical expected weight of silver bromide, based on complete reaction of dibromobutane with the silver methanedisulfonate.

The original filtrate was evaporated under reduced pressure, leaving a light brown oil. Washing the oil with methylene chloride turned the oil into a brown gum and a cloudy supernatant. The supernatant was decanted and treated with decolorizing charcoal. Removal of the charcoal by filtration left a colorless, clear solution. The solvent was removed under reduced pressure, yielding small white cubic crystals. The crystals were recrystallized from a 2:1 cyclohexane-methylene chloride mixture. Small white needles were recovered, dried, and weighed. The weight was 0.082 g, representing a 3.79% yield. The product had a melting point at 143-144° C. NMR and IR spectral analysis of the sample showed the spectral characteristic expected for tetramethyl methanedisulfonate. Elemental analysis of the product calculated for $C_5H_{10}O_6S_2$ is: C, 26.08; H, 4.38; S, 27.85. The experimental values were C, 26.08; H, 4.77; and S, 27.66.

EXAMPLE III

Preparation of Trimethylene Methanedisulfonate

Purified 1,3-dibromopropane obtained from Aldrich Chemical Co. (4.76 g, 0.024 mole) was added to a freshly prepared silver methanedisulfonate solution in 100 ml of dry acetonitrile from Example I. The mixture was heated under reflux at 82° for 3 days, after which a yellow-green powder formed. The powder was filtered, washed with dry acetonitrile, filtered, dried and weighed. The dry weight of 5.92 grams represented 65.5% of the expected weight of silver bromide, based on complete reaction of the dibromopropane with silver methanedisulfonate. The solvent from the reflux reaction was removed under reduced pressure, and the remaining oil was treated by the procedure described for the purification of tetramethylene methanedisulfonate in Example II. The small white crystals obtained weighed 0.563 grams, representing an 11% yield, and showed melting points between 156 and 157.5° C. and 185.5 and 186.5° C. NMR and IR spectra of the twice recrystallized compound showed the characteristic features of trimethylene methane disulfonate. The calculated elemental analysis for $C_4H_8O_6S_2$ is C, 22.22; H, 3.72; and S, 29.66. The experimental values were: C, 22.31; H, 3.69; and S, 28.91.

EXAMPLE IV

Preparation of Ethylene Methanedisulfonate

Purified 1,2-dibromoethane obtained from Aldrich Chemical Co. (4.42 g, 0.024 mole) was added to a freshly prepared silver methanedisulfonate solution in approximately 100 ml of acetonitrile, prepared in accordance with Example I. After 4 days of heating under reflux at 82°, the reaction mixture was cooled and filtered. The yellow-green powder thus obtained was washed with acetonitrile, dried, and weighed. The 4.01 gram weight of the dried powder represented 44.5% of the expected weight of silver bromide, based on complete reaction. The filtrate from the reflux reaction was removed under reduced pressure, leaving a light brown viscous oil. The oil was treated with methylene chloride, as in Example II, forming a cloudy white supernatant and an opaque brown gum. The supernatant was decanted and treated with decolorizing charcoal and diatomaceous earth. The solution, after filtering, was clear and colorless. The solvent was removed under reduced pressure leaving small white crystals. These were recrystallized from a cyclohexane-methylene chloride mixture and vacuum dried. The dried weight was 0.113 g, representing a 2.18% theoretical yield, and the melting point was about 170° C. IR and NMR spectra of the recrystallized product showed the characteristic features of ethylene methanedisulfonate. Atomic analysis was in conformity with the values calculated for $C_3H_6O_6S_2$.

The same procedure described above was repeated, using 5.09 g, 0.028 mole of purified 1,2-dibromoethane and a 100 ml solution of silver methanedisulfonate. The reaction was heated under reflux at 82° C. for one day. The yellow-green powder weighed 3.55 g, 0.75 g less than the weight of the expected AgBr. Small white needles having a total weight of 0.162 g, representing a 2.78% yield, were obtained.

EXAMPLE V

Preparation of Methylene Methanedisulfonate

A flask containing approximately 100 ml of silver methanedisulfonate solution was equipped with a reflux condenser and a drying tube. Purified diiodomethane obtained from Aldrich Chemical Co. (5.09 g, 0.019 mole) was added and the solution was heated under reflux for 2 days. A light yellow powder which formed was filtered, washed, and dried, as in Example II. The dried precipitate weighed 5,79 g, representing 72.0% of the weight of the expected AgI. The filtrate was treated as described in Example II to obtain small white needles having a total weight of 0.081 grams, representing a yield of 2.22%, and having a melting point of between 146° C. and 146.5° C. IR and NMR spectral analysis of the white needles, after further recrystallization, showed the features characteristic of methylene methane disulfonate. Elemental analysis calculated for $C_2H_4O_6S_2$ was: C, 12.76; H, 2.14; and S, 34.09, for $C_2H_4O_6S_2$. The measured values were: C, 12.91; H, 2.14; and S, 34.16.

EXAMPLE VI

Preparation of Pentamethylene Methanedisulfonate

The present example and following Examples VII-XII detail the synthesis of cyclic alkane disulfonic esters by the reaction of an alkane disulfonyl chloride with diols of the type: $HO—(CH_2)_n—OH$ where n=2, 3, 4 or 5.

Dimethyl ether of ethylene glycol (glyme) obtained from Burdick and Jackson Laboratories was purified by distillation over sodium and benzophenone. A solution of 1,5-pentanediol obtained from Aldrich Chemical Co. (12.5 g, 0.12 mole) in 350 ml of purified glyme was stirred in a 3-neck 1 liter round bottom flask equipped with a stirrer and a thermometer. The reaction flask was maintained at a temperature of −20° C. by a dowanol-dry ice bath. Methanedisulfonyl chloride, prepared according to the method described by M. Fild and H.P. Rieck, Chem. Zeitung, 109(9):391, (1976), (25.6 g, 0.12 mole), dissolved in 25 ml of glyme, was slowly added through a 60 ml dropping funnel. A solution of triethylamine obtained from Eastman Organic Chemicals (Rochester, NY) (24.3 g, 0.24 mole) in 125 ml of glyme was added dropwise to the vessel over a one hour period. Care was taken to avoid contact with water by covering the dropping funnels with drying tubes filled with $CaCl_2$. Once all additions were completed, the reaction mixture was allowed to return to room temperature and stirred for two hours.

The reaction mixture was vacuum filtered to remove the solid triethylamine hydrochloride. The solid amine hydrochloride residue, which was washed with glyme and then allowed to dry, weighed 37.0 g, representing a 104% calculated theoretical yield. The filtrate was roto-evaporated below 37° C. to remove the glyme. The residue was redissolved in 100 ml of methylene chloride and washed with the following series of cold, aqueous washes: (a.) three times with 30 ml of 5% sodium bicarbonate; (b.) one time with 30 ml of distilled water; and (c.) three times with 30 ml of 5% hydrochloric acid. These wash solutions were cooled to 4° C. to minimize product hydrolysis. The final organic layer was dried over $MgSO_4$ and the methylene chloride was removed by roto-evaporation. The crude product was redissolved in a minimal amount of methylene chloride. Cyclohexane was added until the mixture turned cloudy. The cyclohexane/methylene chloride mixture was placed in a refrigerator for one month and additional cyclohexane was added to the mixture periodically as the mixture cleared, to promote product crystallization. The white powder which formed was filtered and dried. A total amount of 0.22 grams, representing a 6.75% yield of the crystallized product, was obtained. The product decomposed at between 102° C. and 105° C. and was identified by characteristic $CH_2$ and $SO_2$ IR characteristics and $CH_2—(SO_2)_2$, $CH_2—O$ and $—CH_2—$ proton NMR characteristics.

EXAMPLE VII

Preparation of Ethylene Methanedisulfonate—Method 2

Tetrahydrofuran, obtained from Burdick and Jackson Laboratories was freshly distilled from sodium benzophenone according to standard procedure. A solution of ethylene glycol obtained from Aldrich Chemical Co. (1.24 gram) in 200 ml tetrahydrofuran was added to a 500 ml 3-neck flask filled with a 50 ml pressure-equalizing dropping funnel connected to a drying tube, a mechanical stirrer and a low temperature thermometer. The solution was cooled to −20° C. and 4.26 gram (0.02 mole) of methanedisulfonyl chloride in 50 ml tetrahydrofuran was added from the dropping funnel over a period of 15 minutes. Collidine, obtained from Eastman Organic Chemicals (4.85 g, 0.04 mole) in 120 ml tetrahydrofuran was then added slowly to the flask over a period of about 1 hour. The reaction mixture was allowed to warm to 10° C. and the collidine hydrochloride which formed was removed by filtration. The filtrate was concentrated on the rotary evaporator at 20 mm pressure. The residue was placed under a high vacuum (1–2 mm) for about 15 minutes, then 50 ml of cold 5% HCl was added and the mixture was placed in the refrigerator overnight. Filtration, followed by vacuum drying, produced 1.02 g, representing a 25% yield of the ethylene glycol ester of methanedisulfonic acid, m.p. 165–69° C. The identity of the product was confirmed by IR and proton NMR spectra.

EXAMPLE VIII

Preparation of Ethylene Methanedisulfonate

Method 3

In a modification of the method described in Example VII, glyme was used in place of tetrahydrofuran and triethylamine, in place of the collidine. The triethylamine hydrochloride was not filtered and the final reaction solution was evaporated under vacuum, and the residue was taken up in ice cold water and filtered to give 4.67 g. (57% yield) of ethylene methanedisulfonate from 0.04 mole of methanedisulfonyl chloride. This product was further purified by vacuum sublimation at 0.5 to 1.0 mm of Hg in a bath heated to 95° C.–102° C. Sublimation removed one of the impurities noted in the NMR spectrum. The sublimed material was submitted for biological testing.

EXAMPLE IX

Preparation of Trimethylene Methanedisulfonate

Method 2

The procedure described in Example VIII, substituting 1,3-propanediol for ethylene glycol, was followed with glyme as the solvent and triethylamine as the base. The residue, after evaporation of the glyme, was taken up in methylene chloride and washed successively with sodium bicarbonate, water, and 5% hydrochloric acid. After drying the methylene chloride over anhydrous magnesium sulfate, cyclohexane was added to induce crystallization. From 25.6 g. (0.12 mole) of 1,3-propanediol and 24.3 g. (0.24 mole) of triethylamine, 2.6 g. (10% yield) of trimethylene methanedisulfonate was obtained. The compound was identified by m.p. at 139° C.–142° C. (dec.), and by IR and NMR spectra.

EXAMPLE X

Preparation of Tetramethylene Methanedisulfonate

Method 2

The same procedure as described in Example VIII, substituting 1,4-butanediol for ethylene glycol, was used, and from the same molar quantities of reagents there was obtained a 7% yield of the ester, identified by m.p. 135° C.–136° C. (dec.), and by IR and NMR spectra.

EXAMPLE XI

Preparation of Pentamethylene 1,1-Ethanedisulfonate 1,5-Pentanediol (4.17 g, 0.04 mole) was dissolved in 350 ml of glyme in a 1 liter round bottom flask and the solution brought to −20° C. 1,1-ethanedisulfonyl chloride, synthesized in the same manner as the methanedisulfonyl chloride, (Example I) was dissolved in 25 ml of glyme and this solution added dropwise to the solution in the flask. Triethylamine (8.08 g, 0.08 mole) was dissolved in 125 ml of glyme and this solution was added to the pentanediol/ ethanedisulfonyl chloride solution over a 1 hour period. After the additions were completed, the mixture was brought to 25° C. over a 45 minute period in a water bath. The mixture was roto-evaporated under reduced pressure, at a temperature below 35° C. The residue was washed three times with 20 ml of 5% sodium bicarbonate the resulting emulsion being separated by centrifugation. Water was decanted from the final oil wash, and methylene chloride was added. This solvent apparently dissolved all or most of the impurities, leaving the product suspended in the solution. The product was obtained by vacuum filtering the solution through Whatman #5 qualitative filter papers.

The dried product weighed 0.22 grams, representing about a 2% product yield. The product was identified by characteristic IR and proton NMR spectra. Product decomposition occurred between 141° C. and 142° C. The limited solubility of the compound was confirmed by dissolving 0.03 grams of the dried product in 1 ml acetonitrile and in 1 ml of methylene chloride. In each case, evaporation of the supernatant decanted from the undissolved solid showed that less than 0.01 grams of the pentamethylene ethanedisulfonate product had dissolved in each solvent.

EXAMPLE XII

Preparation of Tetramethylene 1,1-Ethanedisulfonate 1,4-Butanediol, obtained from Aldrich Chemical Co. (3.6 g, 0.04 mole) was dissolved in 75 ml of glyme in a 1 liter round bottom flask. A solution of 1,1-ethanedisulfonyl chloride (9.1 g, 0.04 mole) dissolved in 25 ml of glyme wa added to the flask through a dropping funnel. The reaction mixture was kept below −20° C. with a dowanol-dry ice bath. Triethylamine (8.08 g, 0.08 mole) dissolved in 100 ml of glyme was added to the mixture through a 125 ml dropping funnel over a period of 1 hour. Care was taken to maintain anhydrous conditions by covering the dropping funnels with drying tubes containing $CaCl_2$. The reaction mixture was brought to 25° C. in a cold water bath. The glyme was removed by roto-evaporation, at a temperature below 37° C. The oily yellow residue that remained after removal of the glyme was washed once with 100 ml of 5% sodium bicarbonate and once with 50 ml of cold distilled water, the resulting emulsion being centrifuged immediately to separate the product, and aqueous material decanted. The remaining precipitate was dried under vacuum. The white, powdery solid which remained weighed 0.90 g, representing a 9.2% yield. Product identification was confirmed by characteristic IR and proton NMR spectral features. The product decomposed between 115 and 138° C. The product was soluble to less than about 0.01 gram in 1 ml of either methylene chloride or acetonitrile.

EXAMPLE XIII

Preparation of Trimethylene 1,1-Ethanedisulfonate 1,3-Propanediol obtained from Aldrich Chemical Co. (6.1 g, 0.08 mole) was dissolved in 350 ml of distilled glyme in a 3-neck, 1 liter round bottom flask equipped with a stirrer and a thermometer. The solution was maintained at −20° C. in a dowanol-dry ice bath placed underneath the flask. A solution of 1,1-ethanedisulfonyl chloride (18.2 g, 0.08 moles) dissolved in 25 ml of glyme was slowly added through a 60 ml dropping funnel. Following this addition, a mixture of triethylamine (16.2 g, 0.16 mole) dissolved in 125 ml of glyme was added dropwise to the vessel over a 1 hour period. Care was taken to avoid contact with water by covering the dropping funnels with drying tubes filled with $CaCl_2$. Once all additions were completed, the reaction mixture was brought to room temperature and stirred for 3 hours.

The reaction mixture was vacuum filtered to remove solid triethylamine hydrochloride. The filtrate was roto-evaporated at a temperature below 37° C. to remove glyme. The crude product, having a weight of 7.95 g, was redissolved in a minimal amount of methylene chloride, and cyclohexane was added until the mixture turned cloudy. The initial crystals which formed were removed from solution by vacuum filtration, and additional cyclohexane was added to produce a second crop of crystals, which was also removed by filtration. The two crops of crystals were washed with cold distilled water to remove the surface film of oil. The final weight of solid obtained represented a 36% product yield. The sample decomposed between 151° C. and 155° C., when added to an already heated melting-point apparatus. Product identity was confirmed by IR spectral features related to $CH_3CH$ and $SO_2$, and by proton NMR features related to CH, $CH_2O$, $—CH_2—$ and $—CH_3$.

EXAMPLE XIV

Preparation of Ethylene 1,1-Ethanedisulfonate

The reaction procedure described in Example XIII for the preparation of trimethylene 1,1-ethanedisulfonate was followed, substituting for the 1,3-propane diol used in Example XIII, ethylene glycol (5.0 gram, 0.008 mole). The reaction mixture was stirred for 3 hours at room temperature, the solid amine hydrochloride residue removed, and the filtrate roto-evaporated to remove glyme. The crude product obtained was redissolved in a minimum amount of methylene chloride, and subsequent addition of cyclohexane produced white crystals immediately. Several crops of crystals totaling 5.84 grams were obtained after further addition of cyclohexane and refrigeration. Further recrystallization of the material resulted in a total of 4.37 grams of product, representing a 25.2% yield. The product melting point was between 92° C. and 93° C. Product identification was confirmed by IR spectral features relating to $CH_3CH$ and $SO_2$ and proton NMR features relating to CH, $CH_2$ and $CH_3$.

EXAMPLE XV

Preparation of Sodium 1,2-bis (oxysulfonylmethane sulfonate) Ethane

Methanedisulfonyl chloride, 25.0 g. (0.117 mole), was placed in a 500 ml round-bottom flask containing 200 ml of anhydrous ether. To this stirred solution was slowly added 2.1 g. (0.117 mole) water while the solution was cooled in an ice bath. After the addition of water, the ice bath was removed and the solution was stirred for four hours. The ether was removed by rotary evaporation, and 37 g. (0.35 mole) of freshly distilled trimethylsilyl chloride obtained from PCR Research Chemicals, Inc., (Gainesville, FL) was added slowly, using a bubbler to monitor gas evolution. After the addition of trimethylsilyl chloride, the solution was heated to reflux for several hours until gas evolution ceased. Excess trimethylsilyl chloride was removed by evaporation and the residue was fractionated, giving 24 g. (77%) of trimethylsilyl chlorosulfonylmethanesulfonate, bp. 102° C.-104° C. at 0.2 mm pressure, or 110° C.-111° C. at 0.4 mm pressure. Product identification was confirmed by titration and by NMR spectra.

To a solution of 5.52 g. (0.0207 mole) of trimethylsilyl chlorosulfonylmethanesulfonate in 25 ml. of glyme (freshly distilled from sodium and benzophenane and cooled to −20° C.) was added dropwise a solution of 0.62 g. (0.01 mole) of ethylene glycol and 1.75 g. (0.02 mole) of triethylamine in 25 ml. of glyme. The solution was then allowed to warm to room temperature, filtered, and the glyme removed by evaporation. Two equivalents of sodium bicarbonate in water were added and, after the gas evolution had ceased, the aqueous solution was washed with methylene chloride and then evaporated to leave a white foamy residue containing the sodium salt of 1,2-bis (oxysulfonylmethanesulfonic acid) ethane.

EXAMPLE XVI

Anti-Cancer Activity of Ethylene Methanedisulfonate

Individual strains of mice identified as having the following types of cancer were employed in the present study: lymphocytic leukemia (PS), lymphoid leukemia (LE), melanocarcinoma (Bl), human breast xenograft (MB) and ovarian carcinoma (M5). The left-hand column of Table I below identifies the 6 test systems which were studied, including 2 different lymphoid leukemia groups, identified as LE31 and LE37. For each test system, 6 to 10 animals received a daily dose of ethylene methanedisulfonate, at the doseage indicated in the Dose Range column in the table. The injection route was either intraperitoneal (IP), intracerebral (IC), or subcutaneous (SC), as indicated in the third column from the left in the table. The dose range was that found to be most therapeutically effective against the specified cancer, using the injection route indicated. An equal number of mice received a daily administration of the drug delivery vehicle only (controls).

The control and drug-treated animals were kept on this regimen until all the animals had died, except that in the few cases where the survival time was more than three times that of the control the test animals were designated as cured. The T/C ratio, shown at the right-hand column in Table I, is calculated as the percentage ratio of the median number of days of survival of treated animals (T) divided by the median number of days of control animals (C). Thus, for the PS 31 test system, the T/C value of 270 indicates that the median number of days of survival of treated animals was 270% or 2.7 times the median number of days of survival of untreated animals. In the case of the human breast xenograft test system (MBG5), the T/C ratio provides a measure of the tumor size of treated animals versus that of untreated. The value of 7 means that the tumor of treated animals averaged about 7% of the growth of that of untreated animals.

TABLE I

| Test System | Dose Range | Injection Route | T/C Med. |
|---|---|---|---|
| 3 PS 31 | 25-50 mg/kg | IP | 270 |
| 3 LE 31 | 25-50 mg/kg | IP | 271 |
| 06 LE 37 | 6.25-25.0 mg/kg | IC | 183 |
| 3 B 131 | 12.5-25.0 mg/kg | IP | 166 |
| 3 MB G5 | 50-300 mg/kg | SC | (7) |
| 3 M5 31 (M) | 12.5-50 mg/kg | IP | 217 |
| 3 M5 31 (F) | 25-50 mg/kg | IP | 267 |

The data in Table I show that ethylene methanedisulfonate was effective, at various dose ranges, in treating all five types of cancer studied, and that the drug delivery could be achieved by a variety of injection routes.

EXAMPLE XVII

Anti-Leukemic Activity of Trimethylene Methanesulfonate

A test system corresponding to PS 31 in Table I was carried out to test the effectiveness of trimethylene methanedisulfonate against lymphocytic leukemia. The test protocol was identical to that used in test system PS31 in Example XVI, with the exception that the optimal dose range of between 6.5 and 12.5 mg drug per kilogram body weight was used. The T/C ratio, calculated on the basis of the median number of days survival of treated and untreated animals, was 160, indicating that the drug is effective in the treatment of lymphocytic leukemia, but substantially less so than ethylene methanedisulfonate.

EXAMPLE XVIII

Anti-Leukemic Activity of Tetramethylene Methanedisulfonate

The effectiveness of the tetramethylene methanedisulfonate compound in treating lymphocytic leukemia in a test system like test system PS 31 of Example XVI was examined. The test employed the same general protocol, including the same number of animals and injection route described in Example XVI for test system PS 31, except that the optimal drug dosage for the tetramethylene methanedisulfonate compound of 12.5 to 25 mg per kilogram of body weight was administered. The T/C ratio, calculated on the basis of number of median number days survival of treated and untreated animals, was 188, similar to the results obtained with trimethyl methanedisulfonate.

While the invention has been described with respect to preferred embodiments and specific examples, it will be appreciated that various changes and modifications may be made without departing from the spirit of the invention.

What is claimed is:

1. A cyclic disulfonic ester compound of the form

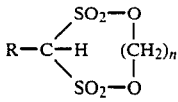

where $n=2-5$ when $R=H$; and $n=2$ when $R=-CH_3$ or $-CH_2CH_3$.

2. The compound of claim 1, wherein $R=H$.

3. The compound of claim 2, wherein $n=2$ or 5.

4. The compound of claim 1, formed by the steps of reacting an alkanedisulfonyl chloride of the form

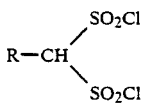

where $R=H$ or $CH_3$, with silver carbonate to form the corresponding silver alkanedisulfonate, and allowing the disulfonate to react with a dihaloalkane of the form

where $X=Br$ or I, and $n=2-5$.

5. The compound of claim 1, formed by the steps of allowing an alkane disulfonyl chloride of the form

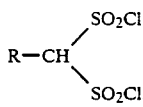

where $R=H$ or $CH_3$, to react with an alkane diol of the form

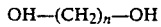

where $n=2-5$, in the presence of tetrahydrofuran or glyme and an aliphatic or aromatic tertiary amine.

6. The compound of claim 5, wherein the tertiary amine is added dropwise to the other reactants at a reaction temperature below about $-20°$ C.

* * * * *